UnitedStates Patent [19]

Stapersma

[11] Patent Number: 4,910,264

[45] Date of Patent: Mar. 20, 1990

[54] COMPLEX-FORMING POLYMERS AND PROCESSES TO PREPARE THEM

[75] Inventor: Johan Stapersma, Amsterdam, Netherlands

[73] Assignee: Shell Oil Company, Houston, Tex.

[21] Appl. No.: 295,615

[22] Filed: Jan. 9, 1989

Related U.S. Application Data

[62] Division of Ser. No. 945,593, Dec. 23, 1986.

[30] Foreign Application Priority Data

Dec. 23, 1985 [GB] United Kingdom ............... 8531625

[51] Int. Cl.$^4$ ................................................ C08F 8/30
[52] U.S. Cl. ................................ 525/333.6; 526/265; 526/259
[58] Field of Search ...................... 526/259, 265; 525/333.6

[56] References Cited

U.S. PATENT DOCUMENTS

| | | | |
|---|---|---|---|
| 3,436,395 | 4/1969 | Ennis et al. | 260/288 |
| 3,810,888 | 5/1974 | Chapuriat | 260/240 D |
| 4,158,093 | 6/1979 | Bailey et al. | 542/455 |
| 4,188,395 | 2/1980 | Bossert et al. | 424/266 |
| 4,424,359 | 1/1984 | Kaschig et al. | 546/255 |

FOREIGN PATENT DOCUMENTS 0216542  4/1987  European Pat. Off. .

OTHER PUBLICATIONS

Three-Phase Test. Detection of Free Cyclobutadiene by Julius Rebek, Jr. and F. Gavina, Sep. 11, 1974.
Poly(styryl)bipyridine: Synthesis and Formation of Transition-Metal Complexes . . . by Roger J. Card and Douglas C. Neckers, 11-23-77.

Primary Examiner—Joseph L. Schofer
Assistant Examiner—Peter D. Mulcahy

[57] ABSTRACT

The invention is a complex-forming polymer comprising at least one aryl group having a 2,2'-bipyridine complex-forming moiety or a 1,10-phenanthroline complex-forming moiety. The complex-forming polymers are prepared by contacting a substituted 2,2'-bipyridine or a substituted 1,10-phenanthroline compound with a metalating agent, and then reacting the metalated compound with an halomethylated polystyrene polymer, or alternatively, reacting the metalated compound with at least one vinylbenzyl halide and subsequently polymerizing the reaction product. The complex-forming polymers are hydrolytically stable and may be used as polymeric ligands as such or complexed with selected metal compounds.

20 Claims, No Drawings

COMPLEX-FORMING POLYMERS AND PROCESSES TO PREPARE THEM

FIELD OF THE INVENTION

This is a divisional of application Ser. No. 945,593 filed Dec. 23, 1986, now issued as U.S. Pat. No. 4,814,457.

The present invention relates to nitrogen-containing complex-forming polymers, and in particular to polymers carrying 2,2'-bipyridine- or 1,10-phenanthroline-based complex-forming moieties. The invention also relates to the preparation of such complex-forming polymers, to novel compounds formed as intermediates in the preparation of the complex-forming polymers, and to the complexed polymers.

BACKGROUND OF THE INVENTION

Nitrogen-containing complex-forming polymers are known. U.S. patent specification 3,810,888 describes complex-forming polymers wherein 2,2'-bipyridine- or 1,10-phenanthroline-based complex-forming moieties are linked via an acetal group to the macromolecular polymer chain of a hydroxyl group-carrying polymer. The complex-forming polymers are the reaction products of a polyvinyl alcohol and 4-(p-formylstyryl)-2,2'-bipyridine or 4-(p-formylstyryl)-1,10-phenanthroline respectively. In the *Journal of the American Chemical Society*, 97 (12), 3454 (1975), polymeric phenanthrolines are described which are prepared by reacting a chlorosulfonated, highly cross-linked polystyrene resin with 5-amino-o-phenanthroline. These complex-forming polymers have in common with the complex-forming polymers of U.S. No. 3,810,888 that the complex-forming moiety is linked to the macromolecular polymer chain via a hydrolytically unstable group.

European Patent Application 45,277 discloses complex-forming polymers having pendant bipyridyl groups as complex-forming moieties, wherein the bipyridyl groups are linked directly to the macromolecular polymer chain. The polymers are prepared by polymerizing a 4- or 6-vinyl-2,2'-bipyridine. These complex-forming polymers have a disadvantage in that the complex-forming complex-forming polymers have a disadvantage in that the complex-forming moieties are situated very close to the polymer chain and hence may be inaccessible or insufficiently mobile.

In *Inorganic Chemistry*, 17 (9), 2345 (1978), polystyryl bipyridines are described. These complex-forming polymers are prepared by lithiating a brominated cross-linked polystyrene and subsequently reacting the lithiated polystyrene with bipyridine. It is reported that just over 50% of the brominated phenyl groups are converted to the corresponding phenylpyridine group. Said process not only has a low yield but moreover may give rise to the formation of multicoupled complex-forming groups.

SUMMARY OF THE INVENTION

A novel class of complex-forming polymers has now been synthesized wherein the 2,2'-bipyridine- or 1,10-phenanthroline-based complex-forming moieties are situated at some distance from the macromolecular polymer chain and are linked to the polymer chain via a hydrolytically stable group. The complex-forming polymers may be non-crosslinked or crosslinked polymers.

The invention provides therefore a polymer having at least one pendant aryl group carrying a complex-forming moiety of general formula

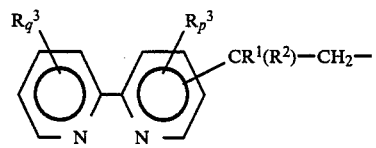

wherein $R^1$ is selected from the group consisting of H and an alkyl group; $R^2$ is selected from the group consisting of H, an alkyl group, a vinylbenzyl group and a group

wherein the moiety —CH—CH$_2$— forms part of a macromolecular polymer chain; each $R^3$ individually is selected from the group consisting of an alkyl, phenyl, alkoxy, phenoxy, alkylthio and phenylthio group; p is an integer from 0 to 2 and q is an integer from 0 to 3; the —CR$^1$(R$^2$)—CH$_2$— group is bonded to a carbon atom of the heterocyclic aromatic ring which occupies the ortho- or para-position with respect to the nitrogen atom in said heterocyclic ring. $R^1$ and $R^2$ together may form a group —(CH$_2$)$_n$—, wherein n is an integer from 2 to 6.

The invention also provides a polymer having at least one pendant aryl group carrying a complex-forming moiety of general formula

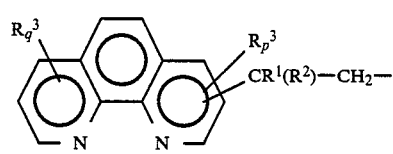

wherein $R^1$ is selected from the group consisting of H and an alkyl group; $R^2$ is selected from the group consisting of H, an alkyl group, a vinylbenzyl group and a group

wherein the moiety —CH—CH$_2$-forms part of a macromolecular polymer chain; each $R^3$ individually is selected from the group consisting of an alkyl, phenyl, alkoxy, phenoxy, alkylthio and phenylthio group; p is an integer from 0 to 2 and q is an integer from 0 to 3; the —CR$^1$(R$^2$)—CH$_2$— group is bonded to a carbon atom of the heterocyclic aromatic ring which occupies the ortho- or para-position with respect to the nitrogen atom in said heterocyclic ring. $R^1$ and $R^2$ together may form a group —(CH$_2$)$_n$—, wherein n is an integer from 2 to 6, when the group —CR$^1$(R$^2$)—CH$_2$— is bonded to the carbon atom which occupies the ortho-position with respect to the nitrogen atom in the heterocyclic aromatic ring.

The invention provides a process for preparing a complex-forming polymer which process comprises contacting a compound selected from the group consisting of compounds of the general formulae

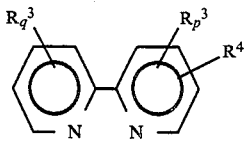

IVa and

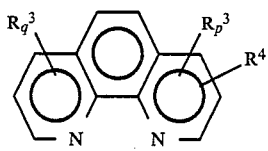

IVb wherein each $R^3$ is individually selected from the group consisting of an alkyl, phenyl, alkoxy, phenoxy, alkylthio and phenylthio group, wherein p is an integer from 0 to 2 and q is an integer from 0 to 3, wherein $R^4$ is bonded to the ortho- or para-position with respect to the nitrogen atom in the heterocyclic ring of general formulae IVa and IVb, $R^4$ is selected from the group consisting of an alkyl group, and a cycloaliphatic group having from 3 to 7 carbon atoms in the ring, $R^4$ has at least one hydrogen bonded to the α-carbon atom, and when $R^4$ is bonded to the para-position with respect to the nitrogen atom of the of the heterocyclic ring of general formula IVb $R^4$ is an alkyl group having at least two hydrogens bonded to the α-carbon atom, with a metalating agent, and reacting the metalated product with an halomethylated polystyrene. Alternatively, the metalated product may be reacted with at least one vinylbenzyl halide and the reaction product polymerized under conditions suitable to prepare a polymer.

The invention also provides a process for the preparation of a compound of the general formulae

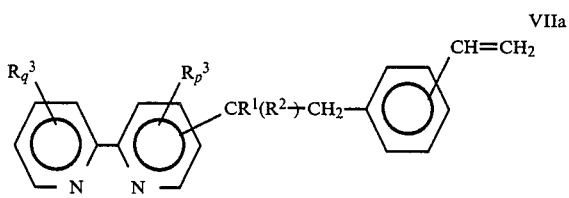

VIIa and

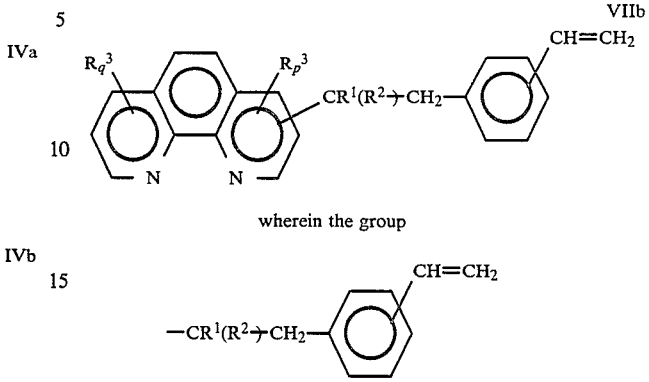

VIIb wherein the group

is bonded to the ortho- or para-position with respect to the nitrogen atom in the heterocyclic ring of general formulae VIIa and VIIb, $R^1$ is selected from the group consisting of H and an alkyl group, $R^2$ is selected from the group consisting of H, an alkyl group, a vinylbenzyl group and a group of the formula

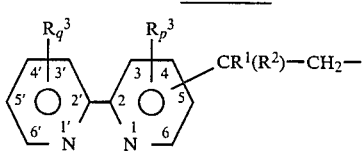

wherein the moiety —CH—CH$_2$— forms part of a macromolecular polymer chain, $R^1$ and $R^2$ together may form a group —(CH$_2$)$_n$—, wherein n is an integer from 2 to 6, unless the group —CR$^1$(R$^2$)—CH$_2$— is bonded to the para-position with respect to the nitrogen atom in the heterocyclic ring of general formula Ib, wherein each $R^3$ is individually selected from the group consisting of an alkyl, phenyl, alkoxy, phenoxy, alkylthio and phenylthio group, wherein p is an integer from 0 to 2 and q is an integer from 0 to 3 which process comprises contacting a compound selected from the group consisting of compounds of the general formulae IVa and IVb with a metalating agent, and reacting the metalated product with at least one vinylbenzyl halide.

The invention also relates to metal complexed polymers prepared by contacting a complex-forming polymer according to the invention with a metal compound under conditions effective for complex-forming.

Structures

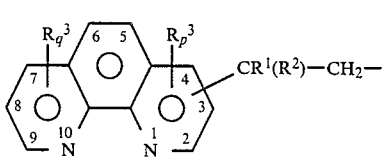

II and

III

Structures

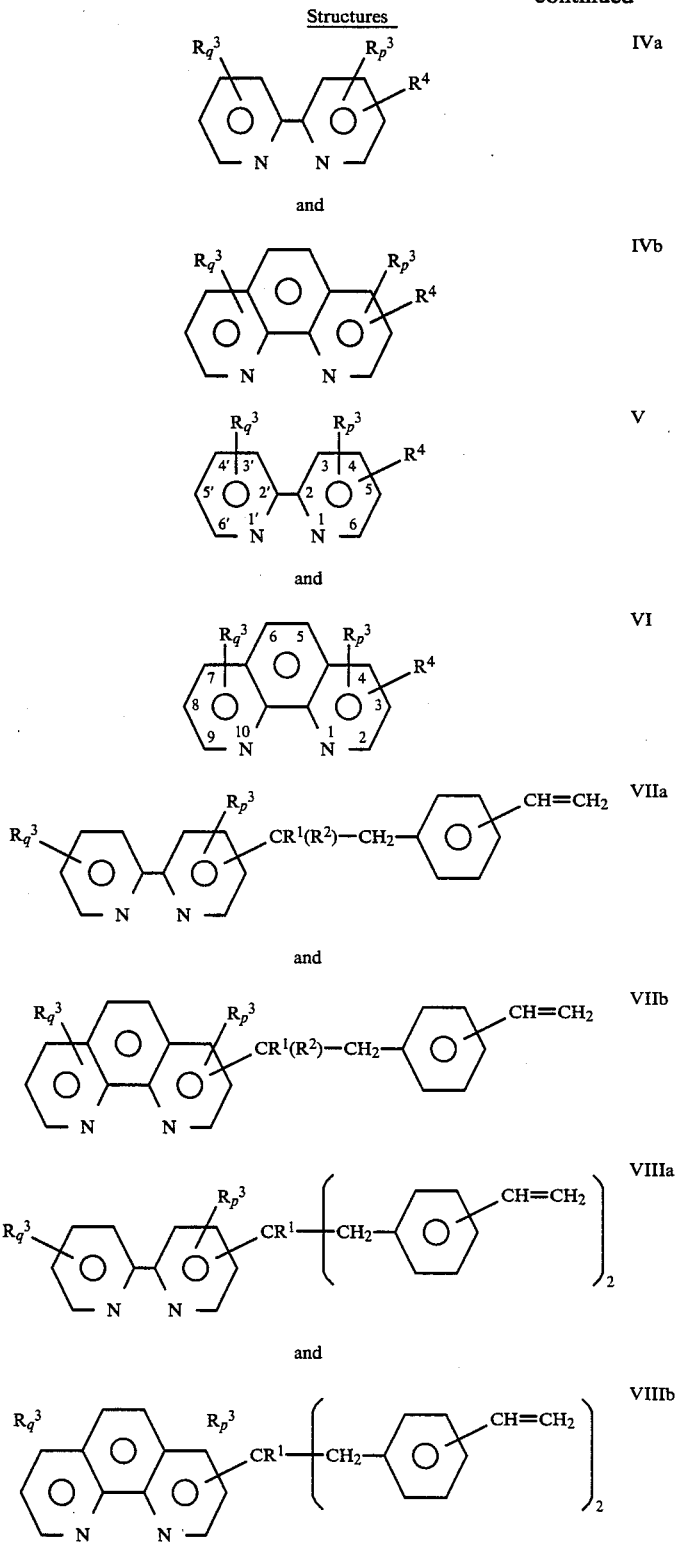

DESCRIPTION OF THE INVENTION

The polymers of the present invention which have at least one pendant aryl group carrying a complex-forming moiety of general formula I, comprise both non-crosslinked and crosslinked polymers. The non-crosslinked polymers having at least one pendant aryl group include homopolymers of monovinylaromatic compounds, copolymers of more than one monovinylaromatic compound and copolymers of at least one monovinylaromatic compound and at least one monoethylenically unsaturated compound. The crosslinked copolymers include copolymers of at least one monovinylaromatic compound and at least one divinylunsaturated compound.

The monovinylaromatic compounds include styrene and analogs and homologs of styrene such as α-methylstyrene, and ring substituted styrenes such as vinyltoluene. Styrene is a preferred monovinylaromatic compound.

Suitable mono-ethylenically unsaturated compounds include monoethylenically unsaturated carboxylic acids such as acrylic acid, methacrylic acid, itaconic acid, maleic acid and fumaric acid; esters of such acids, such as methyl acrylate, ethyl acrylate, butyl acrylate, methyl methacrylate, 2-ethylhexyl acrylate; vinylpyridine and other similar compounds.

The divinyl unsaturated compounds on which the crosslinked polymers, having at least one pendant aryl group may be based, include compounds such as divinylbenzene, divinyltoluene, divinylxylene, divinylpyridine, divinyl ketone, divinyl sulfone; divinyl ethers such as the divinyl ether of ethylene glycol and the divinyl ether of polyethylene glycol; diesters of two moles of a monoethylenically unsaturated carboxylic acid and a diol such as ethylene glycol diacrylate, ethylene glycol dimethacrylate, and polyethylene glycol diacrylate. Divinylbenzene is a preferred divinyl compound.

The preferred non-crosslinked polymers having at least one pendant aryl group are polystyrene and copolymers of styrene and one or more monoethylenically unsaturated compounds. The most preferred non-crosslinked polymer is polystyrene.

Preferred crosslinked polymers having at least one pendant aryl group are copolymers of styrene and divinylbenzene. Especially preferred are styrene/divinylbenzene copolymers wherein divinylbenzene is present in an amount which corresponds with about 0.5 to about 25%w of said copolymer.

In general formula Ia the complex-forming moiety represents a 2,2'-bipyridine-based complex-forming moiety of general formula

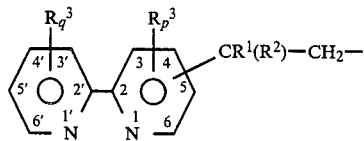

II wherein $R^1$, $R^2$, $R^3$, p and q have the same meaning as in general formula Ia. In general formula Ib the complex-forming moiety represents a 1,10-phenanthroline-based complex-forming moiety of general formula

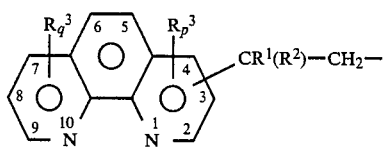

III wherein $R^1$, $R^2$, $R^3$, p and q have the same meaning as in general formula Ib. Hence, in formula II the group —$CR^1(R^2)$—$CH_2$— will be linked to the carbon which occupies the 4- or 6-position and in general formula III to the carbon atom which occupies the 2- or the 4-position in the heterocyclic aromatic ring.

It is preferred that in general formula II and III $R^1$ represents H or an alkyl group having from 1 to 6 carbon atoms and that $R^2$ represents H or an alkyl group having from 1 to 6 carbon atoms, which alkyl group may be the same or different from the alkyl group $R^1$. It is especially preferred that when $R^1$ and $R^2$ represent an alkyl group having from 1 to 6 carbon atoms that said alkyl group is a methyl group. However, when in general formula III the —$CR^1(R^2)$—$CH_2$— group is linked to the carbon atom which occupies the 4-position in the heterocyclic aromatic ring, it is preferred that $R^1$ or $R^2$ represents H.

The heterocyclic aromatic rings in general formula II and III may be substituted by one or more alkyl, phenyl, alkoxy, phenoxy, alkylthio and phenylthio groups. Suitable such alkyl, alkoxy and alkylthio groups include those wherein the alkyl moiety is a linear or branched alkyl group, preferably having from 1 to 6 carbon atoms. Suitable such phenyl, phenoxy and phenylthio groups include those wherein the phenyl group is a ring substituted phenyl group. The number of substituting groups $R^3$ which may be present in general formula II and III is indicated by the value of the integers p, which may vary from 0 to 2 and q, which may vary from 0 to 3. Preferred, however, are polymers wherein in the general formula of the complex-forming moieties p and q are both 0.

The invention also provides a process for the preparation of the previously described novel complex-forming polymers. The process involves a compound of general formula IVa and IVb

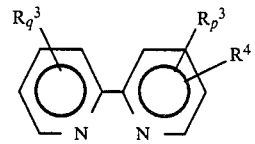

Ia

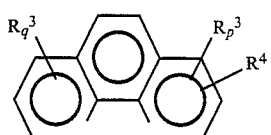

Ib wherein $R^3$, p and q have the same meaning as in general formula Ia and Ib, $R^4$ is an alkyl group, or a cycloaliphatic group having from 3 to 7 carbon atoms in the ring, $R^4$ has at least one hydrogen on the α-carbon atoms, $R^4$ is bonded to a carbon atom of the heterocyclic aromatic ring in the ortho- or para-position with respect to the nitrogen atom of said heterocyclic aromatic ring, and $R^4$ is an alkyl group having at least two hydrogens on the α-carbon atom when $R^4$ is linked to the carbon atom in the para-position with respect to the nitrogen atom in said heterocyclic aromatic ring of formula IVb. Preferably $R^4$ is an alkyl group having from 1 to 6 carbon atoms. The process comprises contacting a compound of general formula IVa or IVb with a metalating agent followed by reacting the metalated compound with at least one vinylbenzyl halide and subsequently polymerizing the reaction product. Alternatively, the process comprises contacting a compound of general formula IVa or IVb with a metalating agent followed by reacting the metalated compound with a halomethylated polystyrene polymer.

General formula IVa represents a 2,2'-bipyridine

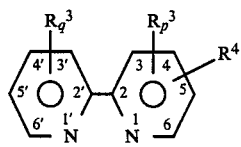

wherein $R^3$, $R^4$, p and q have the same meaning as above and $R^4$ is linked to a carbon atom which occupies the 4- or 6-position in the heterocyclic aromatic ring. General formula IVb represents a 1,10-phenanthroline of general formula

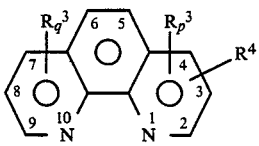

in which $R^3$, $R^4$, p and q have the same meaning as in above and $R^4$ is linked to a carbon atom which occupies the 2- or 4-position in the heterocyclic aromatic ring. Although both general formula V and VI indicate the 2,2'-bipyridine- and 1,10-phenanthroline-based starting compounds may be substituted by a group $R^3$ there is a preference for compounds of general formula V which do not have a $R^3$-alkyl group bonded to a carbon atom in the 4 or 6 and 4' or 6' position, and there is a preference for compounds of general formula VI which do not have an $R^3$ alkyl group linked to the carbon atom in the 2 or 4 and 7 or 9 position. Compounds that are substituted in those positions not only make it more difficult to metalate a specific alkyl group, but moreover there is also the possibility that more than one alkyl group may be metalated. Such multi-metalated compounds may ultimately give rise to the formation of polymers wherein the complex-forming moiety is linked to a macromolecular polymer chain via more than one bond, which could affect the mobility of said complex-forming moiety. Especially preferred are compounds of general formula V and/or VI wherein the integers p and q are 0.

Compounds which may suitably be used in the metalation of the compounds of general formula V and VI include alkali metal compounds. Preferred are alkali metal amides. An especially preferred metalating compound is lithiumdiisopropylamide. The metalating compound is generally employed in a molar ratio of about 1 to 1 with the compound of general formula V or VI and at a temperature in the range of about $-120°$ C. to about $100°$ C., preferably from about $-80°$ C. to about $30°$ C. The reaction is generally carried out in the presence of an inert solvent such as diethyl ether or tetrahydrofuran, mixtures thereof or mixtures thereof with suitable hydrocarbon solvents. THF is a preferred solvent.

The metalated compounds of general formula V and VI may subsequently be reacted with at least one vinylbenzyl halide to arrive at compounds of general formula

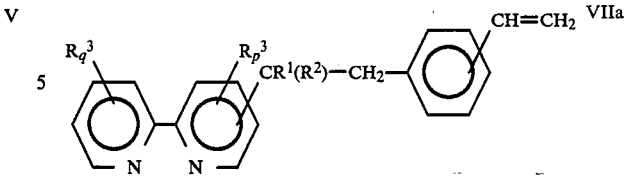

and

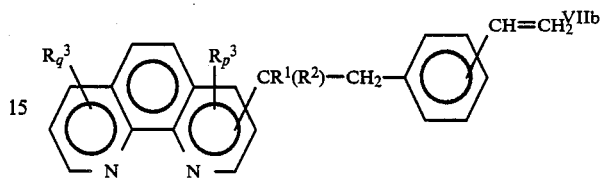

wherein $R^1$, $R^2$, $R^3$, p and q have the same meaning as in general formula Ia and Ib. Vinylbenzyl chlorides are the preferred vinylbenzyl halides. It will be understood by those skilled in the art, that the nature of vinylbenzyl halide used, i.e. o-, m- or p-vinylbenzyl halide, will determine the position of the vinyl group in general formula VIIa and VIIb. Hence, when employing a mixture of e.g. m- and p-vinylbenzyl chloride, the ultimate product will be a mixture of compounds of general formula VIIa or VIIb, having the vinyl group linked to the carbon atom in the 3- or 4-position of the aromatic ring of the vinylbenzylhalide.

During the metalation of compounds of general formula V and VI and the subsequent reaction with an electrophile, it is conceivable that more than one H on the α-carbon atom of $R^4$ may be replaced with a metal atom. When said electrophile is a vinylbenzyl halide this may result in compounds of general formula

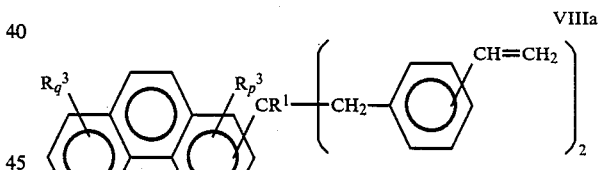

and

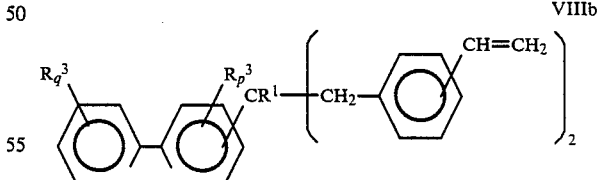

wherein $R^1$, $R^2$, $R^3$, p and q have the same meanings as in general formula Ia and Ib. Hence, in the preparation of compounds of general formula VIIa it is preferred, when $R^4$ in general formula V is alkyl, that the α-carbon atom of $R^4$ carries only one H. It is also preferred in the preparation of compounds of general formula VIIb, if $R^4$ in general formula VI is alkyl, then the α-carbon atom carries only one H when $R^4$ is linked to the carbon atom in the 2-position, and only two H's when $R^4$ is linked to the carbon atom in the 4-position.

The compounds of general formula VIIa, VIIb and VIIIa, VIIIb may be polymerized by known techniques, as such or in the presence of at least one mono- or polyethylenically unsaturated compound, to provide polymers having at least one aryl group carrying a complex-forming moiety of general formula Ia or Ib. When the mixture of polymerizable compounds comprises only compounds of general formula VIIa and VIIb and optionally at least one monoethylenically unsaturated compound, the resulting polymer will be a non-crosslinked homo- or copolymer. When, however, said mixture also includes at least one polyethylenically, preferably diethylenically, unsaturated compound, the resulting polymer will generally be a crosslinked polymer. Crosslinked complex-forming polymers may also be obtained when monoethylenically unsaturated compound such as those of general formula VIIa and VIIb, are polymerized in the presence of a compound of general formula VIIIa and VIIIb.

Suitable monoethylenically unsaturated compounds include monovinylaromatic compounds such as styrene and its analogs nd homologs such as methylstyrene, and ring substituted styrenes such as vinyltoluene; monoethylenically unsaturated carboxylic acids such as acrylic acid, methacrylic acid, itaconic acid, maleic acid, fumaric acid; esters of such monoethylenically unsaturated carboxylic acids such as: methyl acrylate, ethyl acrylate, butyl acrylate, 2-ethylhexyl acrylate, methyl methacrylate, 2-hydroxyethyl methacrylate; vinylpyridine and similar compounds.

Suitable diethylenically unsaturated compounds include compounds such as divinylbenzene, divinyltoluene, divinylxylene, divinylpyridine, divinyl ketone and divinylsulfone; divinyl ethers such as the divinyl ether of ethylene glycol, divinyl ethers of polyethylene glycols; diesters of two moles of a monoethylenically unsaturated carboxylic acid and a diol such as ethylene glycol diacrylate, ethylene glycol dimethacrylate, and polyethylene glycol diacrylate. Divinylbenzene is a preferred diethylenically unsaturated compound.

The homo- and/or copolymerization of the compounds of general formula VIIa and VIIb may be effected by contacting these compounds with e.g. a peroxy-type of radical initiator such as dibenzoylperoxide, cumene hydroperoxide, tert-butylperbenzoate, tert-butylhydroperoxide, peracetic acid, and di-tert-butylperoxide, or with an azotype radical initiator such as α-α-azobisisobutyronitrile (AIBN), 2,2'-azobis(2,4-methylvaleronitrile), 1,1'-azobis(cyclohexane-1-carbonitrile) and 2-α-naphthylazoisobutyronitrile. AIBN is a preferred azo-type radical initiator.

The polymerization of the previously mentioned compounds may also be effected in the presence of a redox type of initiator system. The polymerization will generally be conducted at a temperature in the range of about 0° C. to about 150° C. The amount of initiator or initiator system which may be employed in the present process is not critical and is generally in the range of about 0.01 to 10.0%w on total weight of polymerizable compounds, preferably from 0.01 to 2.0%w. The polymerization may be conducted e.g. in a homogeneous phase which includes both solution and bulk polymerization as well as in an heterogeneous phase which includes emulsion and suspension polymerization. Suitable solvents which may be employed in the solution polymerization, which is a preferred mode, include aromatic hydrocarbons such as benzene, toluene, one or more xylenes; polar solvents such as acetone, methyl ethyl ketone, methyl isobutyl ketone and N,N-dimethylformamide.

An alternative and preferred process route for the preparation of polymers of the present invention is to react the metalated compounds of general formula IV, V and/or VI with a halomethylated, preferably a chloromethylated, polystyrene polymer. Suitable such polystyrenes include both polystyrene homo- and copolymers and also crosslinked polystyrene copolymers. The primary requirement for these polystyrene polymers is that they should be able to carry a halomethyl group, preferably a chloromethyl group. A preferred group of crosslinked polystyrene polymers are the polystyrene (PS)/divinylbenzene (DVB) resins having a DVB content in the range of from about 0.5 to about 25%w. PS/DVB resins are divided into two categories, i.e. the gel-type PS/DVB resins, having a DVB content which is generally not much higher than 2 to 3%w, and the macroporous type of PS/DVB resins having a higher DVB content, generally greater than or equal to 5%w.

Halomethylation, more in particular chloromethylation, of the above described crosslinked resins is well known. Moreover, some types of chloromethylated PS/DVB resins are commercially available, e.g. gel-type chloromethylated PS/DVB resins which are also known as Merrifield resins.

The reaction between the previously mentioned metalated compounds of general formula V and VI and the halomethyl group carrying polymer may conveniently be conducted in the presence of an inert solvent such as diethyl ether or tetrahydrofuran, mixtures thereof, or mixtures thereof with a suitable hydrocarbon solvent and at a temperature in the range of from about $-120°$ C. to about 100° C.

The present invention also relates to the use of the hereinbefore described complex-forming polymers, which use is primarily related to their ability to form complexes with a wide range of metals or metal-containing compounds, i.e. the invention relates to complexed polymers, their preparation, and use.

As the complex-forming moieties of these complex-forming polymers are either 2,2'-bipyridine or 1,10-phenanthroline type complex-forming moieties, it will be understood by those skilled in the art that these polymers may conveniently form complexes with the same metal or metal compounds which also form complexes with the corresponding monomeric bidentate 2,2'-bipyridine or 1,10-phenanthroline ligands; as well as with those metal or metal compounds which are able to form complexes with known complex-forming polymers, having similar types of complex-forming moieties. Suitable complex-forming metals and metal compounds have been outlined in U.S. patent specification 3,810,888 and European Patent Application 0,045,277.

Preferred metal compounds are those based on metals of group VIII and Ib of the periodic table.

The complexes may conveniently be prepared by contacting a solution of a complex-forming polymer with a solution of a suitable metal compound under complex-forming conditions. However, when the complex-forming polymer is insoluble, as may be the case with a crosslinked complex-forming polymer, it may be advantageous to suspend said polymer in a solvent which may simultaneously act as a solvent for the metal compound or is at least (partially) miscible with the solution of the metal compound.

Although the obvious and preferred process route to arrive at complexed polymers of the present invention is to contact the complex-forming polymer with a suitable metal compound, as hereinbefore described, it is also possible to contact a compound of general formula VIIa and VIIb with a suitable metal compound, and subsequently polymerize the resulting complex to arrive at a complexed polymer of the present invention. It is conceivable that this approach may be beneficial e.g. when aiming for crosslinked polymers wherein all possible complex-forming moieties have been complexed, which may not always be possible e.g. when contacting a suitable metal compound with a suspension of crosslinked complex-forming polymer. This method of complex-formation prior to polymerization may also be beneficial in the preparation of complexed polymers having more than one type of complex.

The complex-forming polymers of the present invention are versatile products which may be advantageously used in many applications, such as extraction and separation processes for metals and for metal compounds or in purification processes. Furthermore, these polymers may be conveniently used in the form of their corresponding complexes with a metal or metal compound, as a catalyst or catalyst precursor for reactions such as hydrogenation, dehydrogenation, isomerization, hydroformylation, reductive carbonylation and the like.

The invention will be further understood from the following examples.

PREPARATION OF 4-ethyl-1,10-phenanthroline

In a Schlenk tube reactor equipped with a magnetic stirrer and in an inert atmosphere (argon) 2520 μl 1.6M (4.0 mmol) n-butyllithium solution in n-hexane was added dropwise with the aid of a syringe to a solution of 600 μl diisopropylamine (HDA) in 2800 μl anhydrous tetrahydrofuran (THF) at 0° C. The resulting mixture was stirred for 15 minutes at 0° C. To this mixture a solution of 749.0 mg (3.86 mmol) 4-methyl-1,10-phenanthroline, dissolved in 18 ml anhydrous THF, was added in 5 minutes. The reactor contents were stirred at 0° C. for 1 hour, whereupon 570 mg (4.0 mmol) methyl iodide was added with the aid of a syringe. The mixture was stirred at 0° C. for 45 minutes, after which the external cooling was stopped and reactor contents were allowed to warm to room temperature (18°-20° C.) and stirred at that temperature for 18 hours. Subsequently 1 ml water was added to the reactor and the mixture was stirred for about 5 minutes and transferred into a separatory funnel with the aid of 15 ml water and 100 ml chloroform. After equilibration the organic phase was removed, and the aqueous phase was extracted with 50 ml chloroform. The combined chloroform phases were washed consecutively with 10 ml water and 15 ml brine, and dried over anhydrous magnesium sulfate. The chloroform was removed at 60° C. under reduced pressure (approx. 250 mbar) using a rotary evaporator. The crude product was purified by column chromatography using basic alumina; column diameter and height: 1.7×1.8 cm. After elution with 300 ml of diethyl ether the product was eluted with 200 ml chloroform. The appropriate fraction (yellow band) was collected and the solvent was removed at 60° C. under reduced pressure (approx. 250 mbar) using a rotary evaporator. The residue was sublimed at 120°-180° C. under reduced pressure (0.5 mbar). The pale yellow solid was stored in a dessicator under reduced pressure (1 mbar) over phosphorus pentoxide.

Yield: 645.6 mg (3.1 mmol; 80.4%).

| Analysis for $C_{14}H_{12}N_2$ | | | |
|---|---|---|---|
| calculated | C 80.74% | H 5.80% | N 13.45% |
| found | C 80.54% | H 5.86% | N 13.42% |

EXAMPLE 1

Preparation of a mixture of 4-[1-methyl-2-(3-vinylphenyl)]-ethyl-1,10-phenanthroline and 4-[1-methyl-2-(4-vinylphenyl)]-ethyl-1,10-phenanthroline.

In a Schlenk tube reactor equipped with a magnetic stirrer and in an inert atmosphere (argon) 2520 μl 2.6M (4.0 mmol) n-butyllithium solution in n-hexane was added dropwise with the aid of a syringe to a solution of 600 μl HDA in 2800 μl anhydrous THF at 0° C. The resulting mixture was stirred for 15 minutes at 0° C. To this mixture 799.0 mg (3.84 mmol) 4-ethyl-1,10-phenanthroline prepared following the hereinbefore described method and dissolved in 18 ml anhydrous THF was added in 5 minutes. The mixture was stirred at 0° C. for 2 hours, whereupon 604.8 mg (3.98 mmol) of an approx. 40:60 mixture of para- and meta-vinylbenzyl chloride was added with a syringe. Under continuous stirring the reactor contents were allowed to warm to room temperature (18°-20° C., for 30 minutes and, subsequently, heated for 2 hours at 65° C., after which 1 ml of water was added to the reactor. After 5 minutes the reactor contents were cooled to room temperature and transferred into a separatory funnel with the aid of 30 ml water and 70 ml chloroform. After equilibration the organic phase was separated, and the aqueous phase was extracted with 70 ml chloroform. The combined organic phases were washed twice with 15 ml water, once with 20 ml brine, and dried over anhydrous magnesium sulfate. The solvent was removed at 60° C. under reduced pressure (approx. 250 mbar) using a rotary evaporator. The crude product was purified by column chromatography using basic alumina; column diameter and height: 1.7×20 cm. After elution with 300 ml of diethyl ether the product was eluted with 200 ml chloroform. The appropriate fraction (yellow band) was collected and the solvent was removed at 60° C. under reduced pressure (approx. 250 mbar) using a rotary evaporator leaving a brown oil.

Yield: 1.7 g (3.3 mmol; 86%).

EXAMPLE 2

Polymerization of products prepared in example 1

A mixture of 400.8 mg (1.24 mmol) product was prepared in example 1, 7.7 mg azobisisobutyronitrile (AIBN) and 10 ml anhydrous benzene was introduced into a glass reactor equipped with a reflux condensor, gas inlet and a magnetic stirring device, and degassed three times. Subsequently, the reactor contents heated at 75° C. for 24 hours in an argon atmosphere, after which period of time the reaction mixture was allowed to cool to room temperature. The mixture was diluted with 20 ml chloroform, filtered and concentrated to 4 ml to 70° C. under reduced pressure (approx. 250 mbar) using a rotary evaporator. While stirring the residue was added dropwise to 40 ml diethyl ether. The resulting precipitate was redissolved in chloroform and purified by two further precipitations from methanol.

Yield: 95.3 mg (0.29 mmol; 24%) pale brown solid.

| Analysis for $(C_{23}H_{20}N_2)_n$ | | | |
|---|---|---|---|
| calculated | C 85.15% | H 6.21% | N 8.63% |
| found | C 84.43% | H 6.46% | N 8.54% |

EXAMPLE 3

Prepration of copolymers based on products prepared in example 1 and styrene (method A)

A mixture of 463.8 mg (1,4 mmol) of the product as prepared in example 1, 245 mg (2.4 mmol, styrene, 6.5 mg AIBN, and 11.5 ml anhydrous benzene was introduced into a similar reactor as in example 2 and degassed three times and, subsequently, heated at 75° C. for 24 hours in an argon atmosphere. Next, the reaction mixture was allowed to cool to room temperature, and 10 ml chloroform was added. The mixture was concentrated to 2 ml at 80° C. under reduced pressure (approx. 250 mbar) using a rotary evaporator. While stirring the residue was added dropwise to 40 ml diethyl ether/n-hexane (v/v=1/1). The resulting precipitate was filtered off, redissolved in chloroform and purified by two further precipitations from diethyl ether/n-hexane (v/v=1/1).

Yield: 175.5 mg pale brown solid.

| Analysis for $(C_{23}H_{20}N_2)_q(C_8H_8)_r$ with = 0.29 and r = 0.71. | | | |
|---|---|---|---|
| calculated | C 88.28% | H 6.88% | N 4.84% |
| found | C 87.64% | H 7.06% | N 4.84% |

EXAMPLE 4

Preparation of the reaction product of lithiated 4-ethyl-1,10-phenanthroline and chloromethylated polystyrene (Method B)

In a Schlenk tube reactor equipped with a magnetic stirrer and in an inert atmosphere 315 μl 1.6M (0.50 mmol) n-butyllithium solution in n-hexane was added dropwise with the aid of a syringe to a solution of 75 μl HDA in 300 μl anhydrous THF at 0° C. The resulting mixture was stirred for 15 minutes at 0° C., whereupon 100.6 mg (0.50 mmol) 4-ethyl-1,10-phenanthroline, prepared following the method as hereinbefore described and dissolved in 2.0 anhydrous THF, was added in 5 minutes. The mixture was stirred at 0° C. for 1 hours. After this period of time 200.7 mg chloromethylated polystyrene having a Cl content of approx. 5.1%w, dissolved in 2.0 ml anhydrous THF, was added (soluble chloromethylated polystyrene was synthesized according to J. Gen. Chem. USSR, 38, 2546 (1968) and Helv. Chim. Acta, 56, 1214 (1973)). The resulting mixture was allowed to warm to room temperature (18°–20° C.) for 15 minutes and, subsequently heated at 65° C. for 75 minutes. After the addition of 1 ml of water and stirring for about 5 minutes the mixture was cooled to room temperature and transferred into a separatory funnel with the aid of 5 ml water and 50 ml chloroform.

The organic phase was separated and concentrated to 10 ml at 60° C. under reduced pressure (approx. 250 mbar) using a rotary evaporator. While stirring the residue was added dropwise to a large excess of methanol. The resulting precipitate was filtered off, redissolved in 10 ml chloroform and purified by two further precipitations from methanol.

Yield: 121.1 mg pale brown solid.

Analysis for $(C_{23}H_{20}N_2)_q(C_8H_8)_r(C_9H_9Cl)_s$ with q=0.18, r=0.82 and s=0.

| | | | | |
|---|---|---|---|---|
| calculated | C 89.39% | H 7.12% | N 3.51% | Cl 0.0% |
| found | C 87.10% | H 6.76% | N 3.41% | Cl 0.28% |

In the following examples which are related to the complexation of the polymers of the present invention with some metal compounds, the following abbreviations will be used:

L: polymer of the invention corresponding with one complex-forming moiety.
$L^1$: L based on a polymer as prepred in example 2.
$L^2$: L based on a polymer as prepared in example 3, but containing 62%m styrene.
$L^3$: L based on a polymer as prepared in example 3, but containing 91%m styrene.
Hd: 1,5-hexadiene.
COT: cyclooctene.
2-Me-allyl: 2-methylallyl.
COD: 1,5-cyclooctadiene.

EXAMPLE 5

Preparation of $Rh_2Cl_2(HCOO)_2(L^1)_2$

A 100ml autoclave (Hasteloy C) equipped with a magnetic stirring device was charged with 62 mg (0.27 mmol) $RhCl_2$(2-Me-allyl), (prepared according to H. Pasternak, E. Lancman, and F. Pruchnik, J. Mol. Catal., 29, 13 (1985); F. Pruchnik, Inorg. Nucl. Chem. Lett. 9, 1229 (1973)), 80 mg $L^1$ (0.25 mmol), 20 ml abs. ethanol and 4 ml 98% formic acid. The slurry in the autoclave was purged with argon. Subsequently, the autoclave was sealed and heated for 1 hour at 80° C., followed by 5 hours at 110° C. with vigorous stirring. Next the autoclave was cooled to room temperature, opened, and a dark brown precipitate was filtered off, washed with ethanol and dried. 112 mg of product was isolated. Elemental analysis of said product revealed a complete complexation of the complex-forming moieties, indicating a yield of 89%.

EXAMPLES 6 AND 7

Preparation of $Rh_2Cl_2(HCOO)_2(L^2)_2$ and $Rh_2Cl_2(HCOO)_2(L^3)_2$

Following the same procedure as in Example 5, the corresponding complexes with $L^2$ and $L^3$ were also prepared, employing the same molar ratio of $RhCl_2$(2-Me-allyl) to L. Elemental analysis revealed a complete complexation of the complex-forming moieties.

$Rh_2Cl_2(HCOO)_2(L^2)_2$ was isolated in a 64% yield and $Rh_2Cl_2(HCOO)_2(L^3)_2$ in a 83% yield.

EXAMPLE 8

Preparation of $[Ir(Hd)(L^3)]Cl$

A solution of 40 mg (0.09 mmol) $Ir(COT)_2Cl$ (prepared according to J. L. Herde and C. V. Senoff, Inorg. Nucl. Chem. Lett., 7, 1029 (1971)) in 3.5 ml degassed benzene was purged with argon in a 25 ml Schlenk tube reactor equipped with a magnetic stirring device. While stirring 0.30 ml 1.5-hexadiene was added to this solution and the resulting mixture was stirring at room temperature for 30 minutes, and filtered under argon. To the filtrate 143 mg $L^3$ (corresponding with 0.10 mmol 1,10-phenanthroline moieties) dissolved in 2.0 ml degassed benzene was added under argon. The solution turned purple immediately, and was stirred for 2 hours under argon. The mixture was added to 10 ml diethyl ether and the resulting purple precipitate was filtered off and, after washing with diethyl ether and drying, 132 mg of product was isolated. Elemental analysis revealed a 86% complexation of the complex-forming moieties.

EXAMPLES 9 AND 10

Preparation of [Ir(Hd)(L$^1$)]Cl and [Ir(Hd)(L$^2$)]Cl

Following the same method as in Example 8, the corresponding complexes with L$^1$ and L$^2$ were also prepared, employing the same molar ratio of Ir(COT)$_2$Cl to L. Elemental analysis of the resulting products revealed a complexation of 56 and 69% respectively, for [Ir(Hd)(L$^1$)]Cl and [Ir(Hd)(L$^2$)]Cl.

EXAMPLE 11

Preparation of [Rd(COD)(L$^2$)]ClO$_4$

A solution of 83.6 mg L$_2$ (corresponding to 0.17 mmol 1,10-phenanthroline moieties) in 5.0 ml dichloromethane was added to a magnetically stirred solution of 40.0 mg [Rh(COD)ClO$_4$]$_2$ (prepared according to R. Uson, L. A. Oro, D. Carmona, and M. Esteban, *J. Organometal. Chem.*, 220, 103 (1981)) (containing 0.17 mmol Rh) in 10 ml dichloromethane in an erlenmeyer flask at room temperature. The resulting mixture was stirred at room temperature for 30 minutes. Subsequently, 10 ml diethyl ether was added. The resulting orange-brown precipitate was filtered off, washed with diethyl ether and dried. 123.6 mg of product was collected. Elemental analysis showed complexation of 85%.

EXAMPLES 12 AND 13

Preparation of [Rh(COD)(L$^1$)]ClO$_4$ and [Rh(COD)(L$^3$)]ClO$_4$

Following the same method as in Example 11 the corresponding complexes with L$^1$ and L$^3$ were also prepared, employing the same molar ratio of [Rh(COD)ClO$_4$]$_2$ to L. Elemental analysis of the resulting products showed a complexation of 83 and 82% respectively for [Rh(COD)(L$^1$)]ClO$_4$ and [Rh(COD)(L$^3$)]ClO$_4$.

What is claimed is:

1. A polymer of at least one monovinyl aromatic compound, said polymer comprised of at least one pendant aryl group having a complex-forming moiety selected from the group consisting of moieties having the general formulae

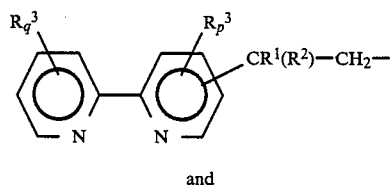

Ia and

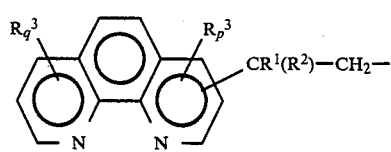

Ib wherein the group —CR$^1$(R$^2$)—CH$_2$— is bonded to the ortho- or para-position with respect to the nitrogen atom in the heterocyclic ring of general formula Ia and Ib, R$^1$ is selected from the group consisting of H and an alkyl group, R$^2$ is selected from the group consisting of H, an alkyl group, a vinylbenzyl group and a group of the formula

wherein the moiety —CH—CH$_2$— forms part of a macromolecular polymer chain, R$^1$ and R$^2$ together may form a group —(CH$_2$)$_n$—, wherein n is an integer from 2 to 6, unless the group —CR$^1$(R$^2$)—CH$_2$— is bonded to the para-position with respect to the nitrogen atom in the heterocyclic ring of general formula Ib, wherein each R$^3$ is individually selected from the group consisting of an alkyl, phenyl, alkoxy, phenoxy, alkylthio and phenylthio group, wherein p is an integer from 0 to 2 q is an integer from 0 to 3.

2. The polymer of claim 1 wherein R$^1$ is an alkyl group having from 1 to 6 carbon atoms.

3. The polymer of claim 1 wherein R$^2$ is an alkyl group having from 1 to 6 carbon atoms.

4. The polymer of claim 1 wherein the integers p and q are 0.

5. The polymer of claim 1 wherein the polymer is a homopolymer.

6. The polymer of claim 1 wherein the polymer is a copolymer.

7. The copolymer of claim 6 wherein the copolymer is a copolymer of a monovinylaromatic compound and a divinyl aromatic compound.

8. The copolymer of claim 7 wherein the copolymer is a copolymer of styrene and divinylbenzene.

9. The copolymer of claim 8 wherein the divinylbenzene is comprises about 0.5 to about 25%w of said copolymer.

10. A polymer as in claim 1 further comprising at least one ethenically unsaturated compound selected from the group consisting of monoethylenically unsaturated carboxylic acids, monoethenically unsaturated carboxylic acid esters, vinylpyridine, divinyl aromatic compounds, divinyl ketone, divinylsulfone, divinyl ethers, and diesters of two moles of a mono ethylenically unsaturated carbocylic acid and a diol.

11. The polymer of claim 10 wherein R$^1$ is an alkyl group having from 1 to 6 carbon atoms.

12. The polymer of claim 10 wherein R$^2$ is an alkyl group having from 1 to 6 carbon atoms.

13. The polymer of claim 10 wherein the integers p and q are 0.

14. The polymer of claim 10 wherein the polymer is a homopolymer.

15. The polymer of claim 10 wherein the polymer is a copolymer.

16. The copolymer of claim 15 wherein the copolymer is a copolymer of a monovinylaromatic compound and a divinyl aromatic compound.

17. The copolymer of claim 16 wherein the copolymer is a copolymer of styrene and divinylbenzene.

18. The copolymer of claim 17 wherein the divinylbenzne is comprises about 0.5 to about 25%w of said copolymer.

19. A complex-forming polymer prepared by a process which comprises contacting a compound selected from the group consisting of compounds of the general formula

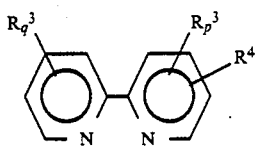

IVa and

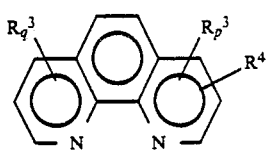

IVb wherein each $R^3$ is individually selected from the group consisting of an alkyl, phenyl, alkoxy, phenoxy, alkylthio and phenylthio group, wherein p is an integer from 0 to 2 q is an integer from 0 to 3, wherein $R^4$ is bonded to the ortho- or para-position with respect to the nitrogen atom in the heterocyclic ring of general formula IVa and IVb, $R^4$ is selected from the group consisting of an alkyl group, and a cycloaliphatic group having from 3 to 7 carbon atoms in the ring, $R^4$ has at least one hydrogen bonded to the α-carbon atom, and when $R^4$ is bonded to the para-position with respect to the nitrogen atom of the heterocyclic ring of general formula IVb $R^4$ is an alkyl group having at least two hydrogens bonded to the α-carbon atom, with a metalating agent, and reacting the metalated product with an halomethylated polystyrene.

20. A complex-forming polymer prepared by a process which comprises contacting a compound selected from the group consisting of compounds of the general formula

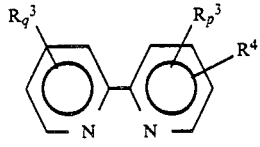

IVa and

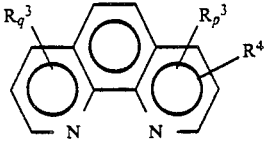

IVb wherein each $R^3$ is individually selected from the group consisting of an alkyl, phenyl, alkoxy, phenoxy, alkylthio and phenylthio group, wherein p is an integer from 0 to 2 and q is an integer from 0 to 3, wherein $R^4$ is bonded to the ortho- or para-position with respect to the nitrogen atom in the heterocyclic ring of general formula IVa and IVb, $R^4$ is selected from the group consisting of an alkyl group, and a cycloaliphatic group having from 3 to 7 carbon atoms in the ring, $R^4$ has at least one hydrogen bonded to the α-carbon atom, and when $R^4$ is bonded to the para-position with respect to the nitrogen atom of the heterocyclic ring of general formula IVb $R^4$ is an alkyl group having at least two hydrogens bonded to the α-carbon atom, with a metalating agent, reacting the metalated product with at least one vinylbenzyl halide and polymerizing the reaction product under conditions suitable to prepare a polymer.

* * * * *